(12) United States Patent
Bakkar et al.

(10) Patent No.: US 10,039,791 B2
(45) Date of Patent: Aug. 7, 2018

(54) PIGMENTABLE EPIDERMIS EQUIVALENT PREPARED FROM MATRIX CELLS AND METHODS FOR THE PRODUCTION THEREOF

(75) Inventors: Khalid Bakkar, Courbevoie (FR); Daniel Asselineau, Bures sur Yvette (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/826,370

(22) Filed: Jul. 13, 2007

(65) Prior Publication Data

US 2008/0097607 A1   Apr. 24, 2008

Related U.S. Application Data

(60) Provisional application No. 60/832,593, filed on Jul. 24, 2006.

(30) Foreign Application Priority Data

Jul. 13, 2006 (FR) ..................................... 06 52984

(51) Int. Cl.
| | | |
|---|---|---|
| A61K 35/36 | (2015.01) | |
| C12N 5/071 | (2010.01) | |
| A61L 27/60 | (2006.01) | |
| A61K 35/12 | (2015.01) | |

(52) U.S. Cl.
CPC .............. *A61K 35/36* (2013.01); *A61L 27/60* (2013.01); *C12N 5/0626* (2013.01); *C12N 5/0629* (2013.01); *C12N 5/0698* (2013.01); *A61K 35/12* (2013.01); *C12N 2501/01* (2013.01); *C12N 2501/11* (2013.01); *C12N 2501/39* (2013.01); *C12N 2502/091* (2013.01); *C12N 2502/092* (2013.01); *C12N 2502/094* (2013.01); *C12N 2502/1323* (2013.01); *C12N 2503/06* (2013.01); *C12N 2533/92* (2013.01)

(58) Field of Classification Search
CPC .. C12N 5/0698; C12N 5/0626; C12N 5/0629; A61K 35/36; A61L 27/60
See application file for complete search history.

(56) References Cited

U.S. PATENT DOCUMENTS

| | | | |
|---|---|---|---|
| 5,266,480 A * | 11/1993 | Naughton et al. ............ | 435/371 |
| 5,639,654 A | 6/1997 | Bernard et al. | |
| 5,667,961 A | 9/1997 | Bernard et al. | |
| 5,861,153 A | 1/1999 | Schmidt et al. | |
| 6,605,466 B1 * | 8/2003 | Pageon et al. ............... | 435/371 |
| 6,974,679 B2 * | 12/2005 | Andre ..................... | A61L 27/24 424/422 |
| 2002/0058337 A1 | 5/2002 | Pageon et al. | |
| 2005/0089512 A1 * | 4/2005 | Schlotmann et al. ....... | 424/93.7 |

FOREIGN PATENT DOCUMENTS

| | | |
|---|---|---|
| EP | 0 418 035 | 3/1991 |
| FR | 2 665 175 A1 | 1/1992 |
| JP | S 64-8974 | 1/1989 |
| JP | S 64-15041 | 1/1989 |
| JP | H 03-151977 | 6/1991 |
| JP | 09-201410 | 8/1997 |
| JP | H 10-118103 | 5/1998 |
| JP | H 11-180878 | 7/1999 |
| JP | 2000-125855 | 5/2000 |
| JP | 2000/350778 | 12/2000 |
| JP | 2000-350778 | 12/2000 |
| JP | 2002-530069 | 9/2002 |
| JP | 2005-176672 | 7/2005 |
| JP | 2005/525088 | 8/2005 |
| JP | 2005-525088 | 8/2005 |
| WO | WO 00/29553 | 5/2000 |
| WO | WO 03/015419 | 6/2003 |
| WO | WO 03/051419 | 6/2003 |
| WO | WO 2005/007835 A1 | 1/2005 |

OTHER PUBLICATIONS

Tobin et al. J Invest Dermatol. 1995, 104:86-89.*
Levy et al. Molecular Biology of the Cell, 2000, 11:453-466.*
Hara et al. Journal of Cell Science, 1994, 107: 2739-2748.*
Stéphane Commo et al., "Melanocyte Subpopulation Turnover During the Human Hair Cycle: An Immunohistochemical Study," 13 Pigment Cell Res. 253-259 (2000).
H.W. Heid et al. *Patterns of expression of trychocytic and epithelial cytokeratins in mammalian tissues I. Human and bovine hair follicles*, 37(2) Differentiation 137-57 (1988).
Alberts, B. et al., Molecular Biology of the Cell, 1158 (3rd ed. 1994) (Exhibit A).
Ovaere P. et al., 34(9) Trends Biochem. Sci. 453-463 (2009) (Exhibit B).
Hensel, W.R. et al., Stedman's Medical Dictionary,1484 (25th ed. 1989) (Exhibit C).
Cotsarelis, G. et al., 57 Cell 201-209 (1989) (Exhibit D).
Schweizer, J. et al., 174(2) J. Cell Biol. 169-174 (2006) (Exhibit E).
Coulombe, P. et al., 109 J. Cell. Biol. 2295-2312 (1989) (Exhibit F).
Michael Detmar et al., Culture of Hair Matrix and Follicular Keratinocytes, 101(1) The Journal of Investigative Dermatology 130S-134S (1993).
Alain Limat et al., Experimental Modulation of the Differentiated Phenotype of Keratinocytes from Epidermis and Hair Follicle Outer Root Sheath and Matrix Cells, 642 Annals New York Academy of Sciences 125-147 (1991).
Alain Limat et al., Phenotypic Modulation of Human Hair Matrix Cells (Trichocytes) by Environmental Influence In Vitro and In Vivo, 2 Epithelial Cell Biology 55-65 (1993).

* cited by examiner

*Primary Examiner* — Vera Afremova
(74) *Attorney, Agent, or Firm* — Buchanan Ingersoll & Rooney PC

(57) ABSTRACT

Epidermis equivalents capable of pigmentation include cells derived from the differentiation of matrix cells; reconstructed skins comprised thereof, optionally containing hair follicles, are useful for evaluating the effect of topical cosmetic, pharmaceutical or dermatological products and may also be used for the preparation of grafts suited to be transplanted on mammals, more particularly on human patients such as victims of third-degree burns.

5 Claims, 2 Drawing Sheets

PIGMENTABLE EPIDERMIS EQUIVALENT PREPARED FROM MATRIX CELLS AND METHODS FOR THE PRODUCTION THEREOF

CROSS-REFERENCE TO PRIORITY/PROVISIONAL APPLICATIONS

This application claims priority under 35 U.S.C. § 119 of FR 06/52984, filed Jul. 13, 2006, and of U.S. Provisional Application No. 60/832,593, filed Jul. 24, 2006, each hereby expressly incorporated by reference and each assigned to the assignee hereof.

BACKGROUND OF THE INVENTION

Technical Field of the Invention

The present invention relates to an epidermis equivalent capable of pigmenting, comprising cells derived from the differentiation of matrix cells, and its method of preparation.

The present invention also relates to a reconstructed skin capable of pigmenting and optionally comprising hair follicles, comprising the said epidermis equivalent, its method of preparation and its use for evaluating the effect of topical cosmetic, pharmaceutical or dermatological products.

The reconstructed skin according to the invention is also useful for the preparation of grafts suited to be transplanted on mammals, more particularly on human patients such as victims of third-degree burns.

Description of Background and/or Related and/or Prior Art

Research and development efforts have been made, for many years, to develop reconstructed skin models which make it possible, on the one hand, to carry out the studies necessary for a better understanding of the role of the skin both in the mechanical field and in the physiological field, and, on the other hand, which constitute predictive tests of the activity of cosmetic and/or pharmaceutical active agents or alternatively of the side effects of topical ingredients.

Thus, it has been possible to develop models that are similar to the human skin to a greater or lesser degree. Exemplary are the models described in EP-0,285,471, EP-0,285,474, EP-0,418,035, WO-A-90/02796, WO-A-91/16010, EP-0,197,090, EP-0,020,753, FR-2,665,175, FR-2,689,904.

In general, the reconstructed skin models described in these references are prepared from fibroblasts of the dermal papilla and/or cells removed from the outer epithelial sheath (also called Outer Root Sheath or ORS) because of the ease of obtaining these cells. Indeed, these cells are removed when a hair strand is pulled and are capable of producing an epidermis when they are deposited on a support, often a dermis equivalent, and cultured in a suitable culture medium.

When the keratinocytes are derived from the ORS, the few melanocytes which may be present in these epidermis models are not many and do not make it possible to obtain a satisfactory pigmented skin model (Lenoir M C, Bernard B A, Pautrat G, Darmon M, Shroot B. Outer root sheath cells of human hair follicle are able to regenerate a fully differentiated epidermis in vitro. *Dev Biol.*, 1988 December; 130(2): 610-20 and Limat A, Breitkreutz D, Hunziker T, Boillat C, Wiesmann U, Klein E, Noser F, Fusenig N E. Restoration of the epidermal phenotype by follicular outer root sheath cells in recombinant culture with dermal fibroblasts. *Exp Cell Res.*, 1991 June; 194(2): 218-27).

With the aim of obtaining pigmented skin models, it is known to add to a keratinocyte culture commercially available epidermal melanocytes (FR-2,665,175). However, the nature of the pigmentation obtained with such a model does not satisfactorily reproduce the natural pigmentation.

The matrix cells, which are located in the hair bulb and form a small cell cluster around the dermal papilla, predominantly consist of precursors of keratinocytes which constitute a germinative layer and which rapidly proliferate and differentiate, forming the hair shaft and thus playing a key role in the hair cycle. From the beginning of the anagen phase up to its end, these matrix cells will proliferate up to the catagen phase and then disappear during the telogen phase (Ebling F J. The biology of hair. *Dermatol. Clin.*, 1987 July; 5(3): 467-81. Review; Saitoh M, Uzuka M, Sakamoto M. Human hair cycle. *J. Invest. Dermatol.*, 1970 January; 54(1): 65-81). The matrix also comprises follicular melanocytes which are responsible for the pigmentation of the hair.

The proliferation and differentiation of these matrix cells are controlled by the dermal papilla (Botchkarev V A, Kishimoto J. Molecular control of epithelial-mesenchymal interactions during hair follicle cycling. *J. Invest. Dermatol. Symp. Proc.*, 2003 June; 8(1): 46-55. Review).

SUMMARY OF THE INVENTION

Surprisingly, it has now been demonstrated that culturing matrix cells on an artificial dermis leads to a complete epidermis comprising, in particular, keratinocytes and melanocytes.

Although the follicular melanocytes present in the matrix are normally useful to color the hair, they are also found to be capable of growing in an epidermal environment and also to be functional for pigmenting epidermis produced in vitro according to the method of the present invention, but also in vivo after grafting. Thus, a novel method has now been developed for preparing a skin model capable of pigmenting exclusively from hair cells, the matrix cells.

This method is found to be advantageous in that it makes it possible to obtain a skin model comprising a complete epidermis by using a single tissue, the matrix, which provides all the epidermal cell types; furthermore, the cells are compatible with each other, in a scarcely differentiated state which allows them to multiply, forming an epidermal tissue which assumes the characteristics of a living epidermis.

This method of preparing an epidermis equivalent does not require a pretreatment designed to enrich the tissue with a given cell type.

The matrix cells may be used regardless of which phase the hair is in: anagen, catagen or telogen.

Finally, this method requires a very small number of cells (about 1,000 cells are inoculated) compared with the techniques already described in the literature using keratinocytes of the ORS (which, for their part, require the inoculation of about 33,000 cells) and the kinetics of colonization of the matrix cells being high, the preparation of the reconstructed epidermis is thereby accelerated.

One difficulty to be overcome is obtaining quality matrix cells in a sufficient quantity.

Under normal conditions, when a hair strand falls or after being pulled out, the dermal papilla-matrix cell compartment remains in the dermis of the scalp. This compartment will initiate the development of a new hair cycle and will give a new follicle. Thus, pulling out a hair strand does not make it possible to obtain these matrix cells, and it will therefore be necessary to carry out a biopsy of the scalp and then isolate these cells by micro-dissection.

In addition to being difficult to isolate, the matrix cells are also difficult to culture at least for the following reasons:
   a) their number is particularly low;
   b) they dissociate easily, it is therefore difficult to locate them during micro-dissection;
   c) they do not adhere to a plastic support;
   d) they are difficult to amplify because they tend to form small colonies and not a primary culture at confluence necessary for the preparation of an epidermis equivalent.

Certain authors have proposed culturing these cells as a co-culture with the fibroblasts of the papilla. The disadvantage of this method is that the culture obtained is not homogeneous, the matrix cells are contaminated with the papilla dermal fibroblasts used in co-culture (Reynolds A J, Lawrence C M, Jahoda C A Human hair follicle germinative epidermal cell culture. *J Invest Dermatol.*, 1993 October; 101(4): 634-8). Luo et al., have proposed a technique for the micro-dissection and culture of matrix cells on a plastic support (Luo et al., Method for culturing hair follicle epithelial matrix cells; Reg. number: H1610; Nov. 5, 1996). However, this micro-dissection technique leads to a very low yield of matrix cells and the culture of these cells only makes it possible to obtain a monolayer of undifferentiated cells which cannot serve as a model for complete skin.

The inventors hereof have isolated matrix cells and developed a method of culturing these cells on a dermis equivalent, these cells proliferate rapidly and differentiate, forming a complete epidermis.

Preferably, the matrix tissue is obtained by a novel micro-dissection technique which preserves the quantity and integrity of the cells; they are not separated from each other. This micro-dissection makes it possible to isolate and preserve all the matrix cells on a dermis equivalent support.

With this dissection technique, the matrix cells adhere more easily to the dermis equivalent, proliferate uniformly and differentiate. The epidermis equivalent obtained may additionally comprise cell types other than keratinocytes such as melanocytes.

The known techniques for preparing epidermis capable of pigmenting use keratinocytes of the ORS to which melanocytes are added following a preculture in vitro; however, a consequence of this preculture is that the differentiation of the cells occurs outside the epidermal context, the melanocytes do not develop a quantity of dendrites comparable to the melanocytes observed in vivo. Their subsequent introduction into the epidermis model does not ensure the homogeneous distribution of the melanocytes in the basal layer of keratinocytes or an optimum functionality of the melanocytes which are generally bipolar (two dendrites) and therefore have a low capacity for transmission of the melanin grains to the keratinocytes.

DETAILED DESCRIPTION OF BEST MODE AND SPECIFIC/PREFERRED EMBODIMENTS OF THE INVENTION

Thus, in a first aspect, the present invention features the use of matrix cells for the preparation of a pigmented epidermis equivalent.

The expression "matrix cells" means the cells located in the hair bulb and they form a small cell cluster around the dermal papilla (Ebling F J. The biology of hair. *Dermatol Clin.*, 1987 July; 5(3): 467-81. Review; Saitoh M, Uzuka M, Sakamoto M. Human hair cycle. *J. Invest Dermatol.*, 1970 January; 54(1): 65-81). Samples of these cells will be collected, amplified and stored in tissue banks.

To preserve the integrity of the matrix tissue, it is possible for these cells to be collected according to the following method: hair follicles are placed in a Petri dish comprising a minimum culture medium supplemented with 2% antibiotic and essential amino acids. The epithelium of the bulb is separated from the dermal papilla and the connective sheath and then the bulbar region is cut at the apex of the dermal papilla. The fragment obtained is then placed on a dermis equivalent inside a sterile ring and then the matrix cells are cultured in a medium detailed in the method of preparing the epidermis below and in Example I.

The matrix cells provide all the cells necessary for the preparation of an epidermis capable of pigmenting; thus, the use of matrix cells for the preparation of an epidermis equivalent does not require any other type of cell and can be carried out with the exclusion of any supply of exogenous cells.

According to a second aspect, the present invention features a method of preparing an epidermis equivalent comprising at least one step for culturing matrix cells on a dermis equivalent.

The "epidermis equivalent"—also designated by epidermis model—obtained according to the method of the invention, is a complete tissue reproducing the characteristics of an epidermis in vivo, namely, a keratinized stratified multilayer epithelium comprising at the very least keratinocytes, with basal cells in contact with a dermis equivalent and whose top strata indicate the terminal differentiation reproducing a histologically normal stratum granulosum and stratum corneum. This epidermis equivalent also comprises functional melanocytes, that is to say, which are capable of transferring melanosomes (melanin grains) to the keratinocytes; histological observation of the epidermis shows organization of the melanocytes at the level of the basal layer, thus accurately reproducing the normal structure of the skin.

Figure 3:
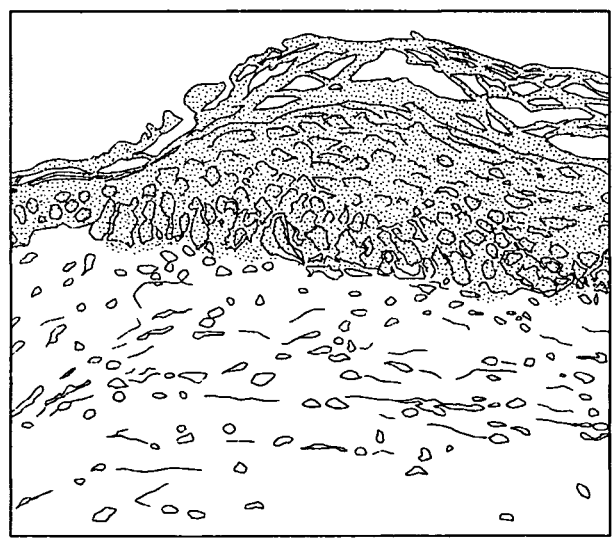

One characteristic of this epidermis model is a large number of melanocytes, containing numerous dendrites (three or more), uniformly surrounding the basal keratinocytes; these characteristics appear very clearly during observation of a cross section of an epidermis model (see in particular FIG. 3 where it is visible that the keratinocytes of the basal layer are surrounded by a thick and dark layer corresponding to the melanocytes).

These characteristics make it possible in particular to distinguish an epidermis model obtained according to the method of the invention in relation to the state of the art methods. Indeed, the epidermis prepared according to conventional methods (subsequent addition of melanocytes) contain a small number of melanocytes, positioned from basal keratinocytes and with two dendrites.

Preferably, the dermis equivalent also comprises Langerhans' cells and/or Merkel cells.

Furthermore, this epidermis is capable of uniformly pigmenting.

Indeed, it appears that the epidermis model according to the invention has a homogeneous pigmentation with melanin grains regularly positioned in the top pole of the keratinocytes and in the stratum corneum. This distribution is advantageous compared with the prior art epidermis models which, for their part, have fewer melanin grains irregularly distributed in the epidermis.

More specifically, the method according to the invention comprises:

a. the inoculation of matrix cells on a dermis equivalent resting on a support immersed in a culture medium;

b. the multiplication of the matrix cells at the surface of the said dermis equivalent;

c. the elevation of the said support such that the culture medium does not cover the top face of the epidermis equivalent during production.

In particular, the support may be a support grid.

The "dermis equivalent", or dermal support, according to the invention may be any one of those described in the prior art (in particular those described in FR-2,665,175). By way of example, representative are, as support, contracted collagen/fibroblast lattices, previously de-epidermized dermis (Prunieras et al., Ann. Chir. Plast., 1979, 24, No. 4, 357-362), an inert support selected from the group consisting of a synthetic semi-permeable membrane (in particular those described in FR-2,833,271), artificial membranes such as, for example, filters of the Millipore trade mark, collagen-based subcutaneous substitutes, or any other air-exposable support compatible with cell viability and adhesion.

Preferably, the dermis equivalent will consist of a collagen lattice in which dermal fibroblasts are distributed which are in a state of differentiation equivalent to that observed in vivo.

This type of dermis equivalent may be prepared according to various methods, for example as described in EP-0,418,035, WO 00/29553 or EP-0,285,471.

This method may comprise the following culture stages:

a) contractile cells harvested, for example, from monolayer cultures produced on a nutrient medium inoculated with fragments of animal or human tissue with b) a nutrient medium supplemented with components of the extracellular matrix of the dermis, the said mixture forming a gel which contracts, expelling the nutrient medium and forming the dermis equivalent.

It is possible to employ fibroblasts as contractile cell; dermal fibroblasts obtained from healthy human donors and harvested from monolayer cultures by controlled trypsinization are advantageously used as contractile cells. As explained below, the choice of contractile cells will determine the differentiation of the matrix cells; they will therefore be selected according to the quality of epidermis equivalent desired.

Matrix cells constitute a reservoir of pluripotent cells that are capable, according to the cellular context created by the dermis equivalent, of forming skin or hair because the fibroblast of the dermis equivalent can direct the keratinocyte differentiation program.

Thus, if the dermis equivalent on which the matrix cells rest predominantly contains inter-follicular skin fibroblasts, because of the interaction from the fibroblasts and the keratinocytes of the matrix, the keratinocytes of the matrix will form an inter-follicular epidermis equivalent.

The skin fibroblast may be a papillary or reticular fibroblast or a combination of both.

For the preparation of an epidermis model capable of pigmenting, an inter-follicular fibroblast may be used.

The method of preparation according to the invention entails inoculating the dermis equivalent—or dermal substrate—with matrix cells.

Whole matrices are deposited on the dermis equivalent. The number of matrices deposited depends on the surface area of the dermis equivalent. For example, when the dermis equivalents are prepared in a 60 mm dish, they have, after contraction, a surface area of about 2 $cm^2$ and are inoculated with about 10 matrices.

Conditions are maintained which allow the multiplication of the matrix cells at the surface of the said substrate, the development of this matrix cell culture being promoted by the use of at least one minimum nutrient medium, preferably a 3F medium as described in Example I in contact with the said matrix surface.

Advantageously, after inoculation of the matrix cells on the substrate, the implanted substrate immersed in this nutrient medium which covers the matrix cells is preferably maintained from 5 to 6 days.

Next, the dermis equivalent is placed in contact with air; for that, it is placed on a support grid which is raised relative to the base of the container and the nutrient medium level is adjusted so that the support grid is just covered but that the nutrient medium does not cover the top surface of the skin equivalent being produced.

According to one embodiment, the method according to the invention may further comprise an additional step intended to induce pigmentation of the epidermis equivalent. This may be a stimulation with UV rays.

The skin equivalent according to the invention thus formed is well differentiated and well organized. It is also homogeneous overall.

The expression "skin equivalent", also designated reconstructed skin below, means the epidermis equivalent combination resting on a dermis equivalent.

The dermis equivalent thus prepared comprises at least keratinocytes and melanocytes.

The epidermis equivalent may also comprise Langerhans' cells and/or Merkel cells; these cells may in particular be added to the support during inoculation of the matrix cells.

According to one embodiment of the method according to the invention, it is possible to prepare a skin equivalent capable of reconstituting one or more hair follicles using a dermis equivalent comprising dermal papilla fibroblasts and/or connective sheath fibroblasts and/or whole dermal papillae.

If the choice is made to include in the dermis equivalent hair fibroblasts such as papilla fibroblasts or connective sheath fibroblasts or the whole papilla or the connective sheath or connective sheath fractions (Reynolds A J, Lawrence C M, Jahoda C A Human hair follicle germinative epidermal cell culture. J. Invest. Dermatol., 1993 October; 101(4): 634-8), because of the interaction from these fibroblasts and the matrix cells, the keratinocytes will reproduce the morphogenesis of the body hair or of the head hair (hair shaft).

The present invention also features an epidermis equivalent capable of pigmenting, comprising cells derived from the proliferation and the differentiation of matrix cells.

This model can be identified by virtue of its histological characteristics: it comprises small melanocytes comprising three or more dendrites surrounding the basal keratinocytes.

It is more specifically an epidermis equivalent prepared according to the method of the invention, the epidermis equivalent has the characteristic feature of being able to pigment uniformly and homogeneously, reproducing the pigmentation of a healthy skin both in vitro and in vivo after grafting.

The pigmentation of the skin or epidermis model (synthesis of melanin by the melanocytes) can be quantified by any known method, in particular by a so-called Fontana Masson staining.

By way of example, and without limitation, the pigmentation can be observed and/or quantified by:

measuring the number of melanin grains in a number of stained vertical sections by computer-aided image analysis;

measuring the melanin content of culture homogenates by biochemical techniques;

measuring the epidermal tyrosinase activity contained in cultures by biochemical techniques;

measuring the number of melanocytes present and their location in cultures by staining with DOPA, by indirect immunofluorescence or electron microscopy techniques;

instrumental measurement of color by colorimetry which takes into account the variable equilibrium from the various pigments and their physicochemical states;

any other technique which makes it possible to accurately evaluate the intensity of the pigmentation obtained.

The inventors hereof have also been able to demonstrate that after grafting, the epidermis equivalent advantageously has this capacity to pigment. Furthermore, the pigmentation obtained is homogeneous, uniform and identical to that of the original skin.

According to another aspect, this invention features a kit for preparing an epidermis equivalent, comprising matrix cells.

This kit may additionally comprise a device comprising a dermis equivalent resting on a support and a nutrient medium suitable for the multiplication and the differentiation of the matrix cells.

According to another aspect, this invention features a kit for evaluating the cosmetic or therapeutic compounds of the skin, comprising an epidermis equivalent obtained according hereto.

Regardless of the method selected for the preparation of the skin equivalent, the epidermis and/or skin equivalent is a three-dimensional model that is useful as an alternative test for all the tests that would require animal experiments, for example studies of the release of active agents, of their skin penetration and/or absorption and/or bioavailability, studies of tolerance, compatibility and efficacy of cosmetic, pharmaceutical or dermatological active agents and/or ingredients.

The epidermis and/or skin equivalent according to the invention may also be used in automated methods for screening cosmetic, pharmaceutical or dermatological products for identifying novel active agents.

The skin equivalent according to the invention also allows physiological study of the mechanism of skin pigmentation and of the growth of head hair and/or body hair.

As the epidermis equivalent according to the invention reproduces the natural pigmentation of the skin, it is particularly advantageous to test depigmenting active agents, pigmenting active agents and sunscreens.

The applications may prove to be particularly useful for photoaging or aging, in particular when products are sought which are capable of lightening "age spots", or lentigos, or more generally lightening the complexion of the skin.

Epidermis equivalents comprising hair follicles will make it possible to perform in particular kinetics of growth of body hair or head hair and therefore any study requiring numerous living hairs which are as complete as possible in an in vivo context such as the study of the hair cycle and of factors capable of influencing this cycle, ranging up to the study of active agents promoting hair growth, of active agents which make it possible to combat hair loss or of active agents which slow the growth of body hair.

By virtue of the presence of active melanocytes, this model also allows the study of active agents which can influence the color of head hair and/or of body hair, in particular by the induction or inhibition of melanin production.

Finally, this model also makes it possible to study the effect of active agents intended to modify the structure of body hair and/or of head hair.

The methods of screening a product in order to identify novel active agents comprise a step (a) for bringing the said test product into contact with an epidermis equivalent according to the invention, and then a step (b) for reading the effect of the product on the epidermis equivalent.

According to one embodiment of the screening method according to the invention, a complete skin model will be used.

Preferably, for carrying out step (a), the test product will be applied topically, for example formulated in conventional topical formulations or introduced in the culture medium.

Depending on the desired effect, step (b) may entail, without being exhaustive, in comparing with an epidermis equivalent according to the invention that has not been in contact with the test product (control) and/or in observing a variation in the intensity of the pigmentation or depigmentation of the epidermis equivalent, optionally by labeling and quantification of melanin (for example by staining according to the Fontana Masson method), an acceleration or a reduction in the growth of the hair shaft, optionally an effect on the production of the hair keratins.

Step (b) may also be carried out by analyzing epidermal and/or dermal markers such as structural proteins, in particular macromolecular and epidermal differentiation proteins of the dermal matrix.

The parameters measured on the epidermis or skin equivalents brought into contact with the test product will be compared with those measured on the control epidermis or skin equivalents cultured under the same conditions but which will not have received the test product.

When the epidermis or skin model comprises cells of the immune system, the Langerhans' cells, the screening tests may also be useful to identify products capable of inducing irritations or allergic reactions.

For that, the parameters observed in step (b) of the screening method will be selected from:

the cytotoxicity;

the release of inflammation mediators;

the cellular damage revealed by histology or by the release of lactate dehydrogenase (a marker for keratinocyte membrane integrity) (Roguet et al *J. Tox. In vitro* 6: 303 (1992) and Ponec M in *In Vitro Toxicology*. Eds Rougier, Maibach and Golberg p. 107, 1994);

the modification of the synthesis and of the composition of skin lipids, particularly ceramides and phospholipids (JID 86, 598 (1986));

the stratification of the epithelial cells as a marker for their differentiation (M Prunieras & R Roguet, *Toxicologie cellulaire in vitro methodes & applications*, Eds M Adolphe, A Guillouzo and F Marano eds INSERM 1995 p. 191-236) (DUFFY P A, FLINT O P: In vitro dermal irritancy test. In C K Atterwill and C E Steele (Eds): In vitro methods in Toxicology Cambridge Univ. Press Cambridge 1987, pp. 279-297) (Use of skin cell culture for in vitro assessment of corrosion and cutaneous irritancy, Roguet, Cell Biology and Toxicology, 1999: 15, 63-75).

The epidermis equivalent will also find applications for the preparation of grafts intended to be transplanted on patients having a skin disorder such as a burn, a wound healing defect, a skin ulcer, psoriasis, a pigmentation disorder such as vitiligo, canities.

The application will also relate to any pathology resulting in serious pigmentation abnormalities for which a correction by grafting may be envisaged, for example congenital or acquired hypomelanosis or hypermelanosis (Na G Y, Seo S K, Choi S K. Single hair grafting for the treatment of vitiligo. *J. Am. Acad. Dermatol.,* 1998 April; 38(4): 580-4), accidental causes, for example skin which has been burnt over a large area of the body or face (for example: victims of third-degree burns); surgical causes, for example skin which has undergone excision for treatment of a nevus (Kumagai et al., *Ann. Plast Surg.,* 39: 483-488, 1997), or of a tatoo (Kumagai et al., *Ann. Plast. Surg.,* 33: 385-391, 1994).

The application also relates to disorders linked to denaturation of the matrix.

The skin equivalent according to the invention also makes it possible to produce autografts when it is prepared from scalp fragments after extraction by micro-dissection of the hair matrices, leading to the rapid formation in vivo of a uniformly pigmented epidermis. These autografts may concern ulcers but also serious burns (Limat A, French L E, Blal L, Saurat J H, Hunziker T, Salomon D. Organotypic cultures of autologous hair follicle keratinocytes for the treatment of recurrent leg ulcers. *J. Am. Acad. Dermatol.,* 2003 February; 48(2): 207-14).

In this specific case, the reconstructed skin also makes it possible to produce multiple microautografts in patients suffering from vitiligo so as to repigment the areas deficient in coloration, under better conditions than the existing ones using cells of the ORS containing few melanocytes.

For all these applications, the skin equivalent according to the invention has the advantage of pigmenting naturally. The grafted skin area is thus more aesthetic and reproduces normal physiological behavior during exposure to the sun.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example I—Preparation of a Pigmented Skin Model

Asselineau D, Bernard B, Bailly C, Darmon M. Epidermal morphogenesis and induction of the 67 kD keratin polypeptide by culture of human keratinocytes at the liquid-air interface. *Exp. Cell Res.,* 1985 August; 159(2): 536-9.

Asselineau D, Bernard B A, Darmon M. Three-dimensional culture of human keratinocytes on a dermal equivalent A model system to study epidermal morphogenesis and differentiation in vitro. *Models dermatol.,* vol. 3, pp. 1-7 (Karger, Basel 1987).

I-A—Preparation of the Dermis Equivalent:

The fibroblasts are thawed, cultured in medium for fibroblasts (MEM+10% of FCS (foetal calf serum) and trypsinized.

For the production of the lattices, the cells are used at confluence from 12 and 13 days after thawing and are prepared so as to obtain a cell suspension in MEM Hepes 10% FCS at $2 \times 10^6$ cells/ml.

Preparation of the Culture Media:
 MEM 1.76×:
MEM 10×17.6 ml
NaHCO3 7.5%, i.e., 5.1 ml
1.76 mM L-Glutamine, i.e., 0.88 ml
0.88 mM Sodium Pyruvate, i.e., 0.88 ml
0.88× non-essential amino acids, i.e., 0.88 ml
8.8 U/8.8 µg/ml (0.088%) Penicillin Streptomycin, i.e., 0.088 ml
0.04×(0.04%) antimycotic antibiotic, i.e., 0.044 ml
Sterile ultra-pure water 75 ml
 MEM Hepes 10% FCS:
MEM 25 mM Hepes 50 ml
2 mM L-Glutamine, i.e., 0.5 ml
1 mM Sodium Pyruvate, i.e., 0.5 ml
1× non-essential amino acids, i.e., 0.5 ml
20 U/20 µg/ml (0.2%) Penicillin Streptomycin, i.e., 0.1 ml
0.1×(0.1%) antimycotic antibiotic, i.e., 0.05 ml
10% FCS, i.e., 5 ml
 NaOH 0.1N:
10 ml NaOH 1N
90 ml sterile ultra-pure water
 This solution is passed through a Millipore filter with a 0.22 µm GV Duropore membrane.
 Acetic Acid 1/1000:
0.5 ml glacial acetic acid 100%
499.5 ml sterile ultra-pure water
 Preparation of the Lattices:
Use of Gattefossé collagen
3.22 ml MEM 1.76×
0.63 ml FCS
0.35 ml NAOH 0.1N
0.2 ml MEM Hepes 10% FCS
Volume=4.4 ml
 To this solution add 0.5 ml of cell suspension.
 Then slowly introduce the required volume of cold collagen.
 Empty the contents of the Erlenmeyer flask into a bacteriological dish Falcon Ø 60 mm.
 Place the dish in an incubator (37° C.-5% $CO_2$) for about 1 h 30 min-2 h.
 Allow the contraction to proceed for 3 days.
 Then inoculate the matrix cells.

Figure 1:
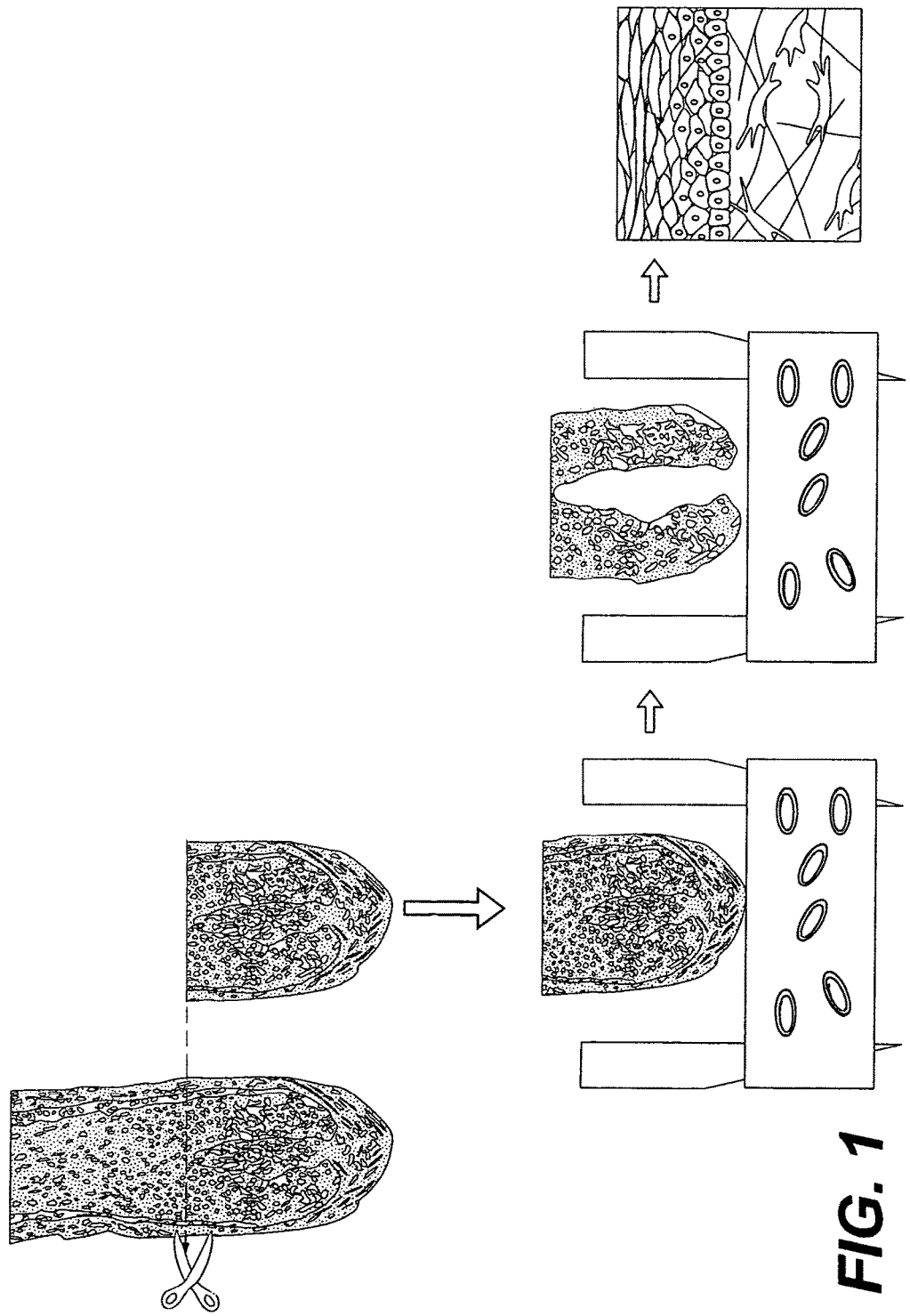
FIG. 1 is a schematic showing the microdissection and culture (inoculation) of matrix cells.

I-B—Microdissection and Culture (Inoculation) of the Matrix Cells (FIG. 1):

From a skin biopsy, a microdissection of the hair follicles is performed and they are placed in a Petri dish containing culture medium. The epithelium is separated from the dermal papilla bulb and the connective sheath and the bulbar region is cut at the apex of the dermal papilla; this fragment is then placed on the dermis equivalent inside a sterile ring by exerting a light pressure with the aid of a needle. The separation of the connective sheath with the matrix cells occurs more easily without the use of proteolitic enzymes, the dermal part is therefore removed and the matrix cells are cultured with the 3F culture medium for one week.

I-C—Production of the Reconstructed Skin:

After 7 days of immersed culture, the skins are placed in emersion. Check however that the keratinocytes leave the lattice by observing under a microscope.

In a Falcon bacteriological dish, place an emersion grid.
 Add 7.5 ml MEM 10% FCS+3 F, avoiding the formation of bubbles.
 Cut out the glue around the skin to be emersed with the aid of a sterile scalpel.
 Transfer the skin onto the grid with a curved pair of tweezers and a cell lifter.
 Place the dishes in the incubator at 37° C.-5% $CO_2$.
 Change the medium on Wednesday and Friday (7.5 ml MEM 10% FCS+3 F).
 After 7 days of emersion, the skins are ready for use.

Figure 2:
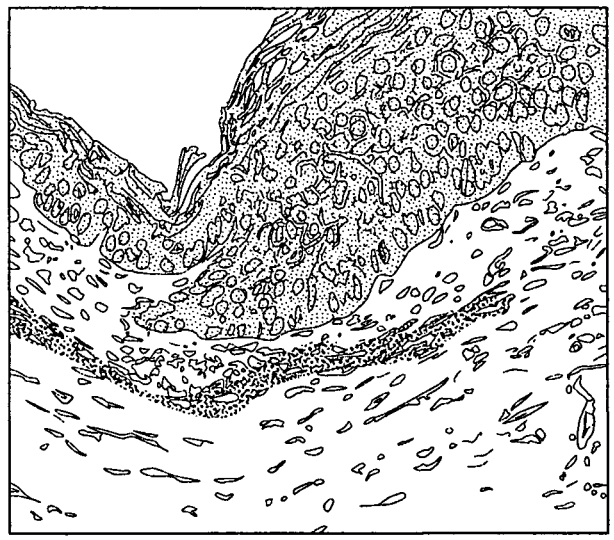
FIGS. 2 and 3 are cross-reactions of reconstructed skin according to the invention.

Culture Medium Used: MEM 10% FCS+3 F:
MEM 500 ml
2 mM L-Glutamine, i.e., 5 ml
1 mM Sodium Pyruvate, i.e., 5 ml
1× non-essential amino acids, i.e., 5 ml
20 U/20 µg/ml (0.2%) Penicillin Streptomycin, i.e., 1 ml
0.1×(0.1%) antimycotic antibiotic, i.e., 0.5 ml
10 ng/ml EGF, i.e., 0.5 ml of the stock solution at 10 µg/ml
10-10 M Cholera Toxin, i.e., 5 ml of the stock solution at 10-5 M
0.4 µg/ml Hydrocortisone, i.e., 0.4 ml of the stock solution at 0.5 mg/ml
10% FCS, i.e., 50 ml FIGS. 2 and 3 represent cross-sections of reconstructed skin according to the method of the invention.

Their observation shows a stratified epidermis surmounted by a stratum corneum reproducing an epidermis in vivo. It is also visible that the epidermis of FIG. 3 comprises melanin.

Example II—Preparation of a Skin Model Comprising a Hair Follicle

The experimental conditions for the protocols described in Example I will be reproduced using follicular fibroblasts in step I-A-.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A man-made reconstructed epidermis consisting essentially of melanocytes having three or more dendrites and keratinocytes, wherein the reconstructed epidermis is prepared by culturing follicular matrix cells on an artificial dermis so that said follicular matrix cells proliferate and differentiate into said melanocytes and keratinocytes on the artificial dermis, and wherein said reconstructed epidermis is not prepared with fibroblasts of the dermal papilla or cells removed from the outer epithelial sheath.

2. A man-made reconstructed epidermis consisting essentially of melanocytes having three or more dendrites, keratinocytes, and optionally Langerhans' and/or Merkel cells, wherein the reconstructed epidermis is prepared by culturing follicular matrix cells and optionally Langerhan's and/or Merkel cells on an artificial dermis so that said follicular matrix cells proliferate and differentiate into said melanocytes and keratinocytes on the artificial dermis, and wherein said reconstructed epidermis is not prepared with fibroblasts of the dermal papilla or cells removed from the outer epithelial sheath.

3. The reconstructed epidermis as defined by claim 1 or claim 2 and having a basal layer, wherein said melanocytes uniformly surround said keratinocytes and wherein said keratinocytes are in the basal layer of said reconstructed epidermis.

4. The reconstructed epidermis as defined by claim 1 or claim 3, wherein the reconstructed epidermis is uniformly pigmented.

5. A man-made skin model consisting essentially of a reconstructed epidermis on an artificial dermis, the reconstructed epidermis consisting essentially of melanocytes having three or more dendrites and keratinocytes, wherein the reconstructed epidermis is prepared by culturing follicular matrix cells on the artificial dermis so that said follicular matrix cells proliferate and differentiate into said melanocytes and keratinocytes on the artificial dermis, and wherein said reconstructed epidermis is not prepared with fibroblasts of the dermal papilla or cells removed from the outer epithelial sheath.

* * * * *